United States Patent
Barenholz et al.

[11] Patent Number: 5,948,756
[45] Date of Patent: Sep. 7, 1999

[54] THERAPEUTIC LIPOPROTEIN COMPOSITIONS

[75] Inventors: Yechezkel Barenholz, Jerusalem; Hilary Shmeeda, Givat Zev; Tova Chajek, Jerusalem, all of Israel

[73] Assignee: Yissum Research Development Company of the Hebrew University of Jerusalem, Jerusalem, Israel

[21] Appl. No.: 08/522,745

[22] Filed: Aug. 31, 1995

[51] Int. Cl.$^6$ ................................................. A61K 38/00
[52] U.S. Cl. ................................... 514/12; 514/2; 514/7; 514/789; 530/352; 530/359; 424/417; 424/450; 424/460
[58] Field of Search ..................... 530/352, 359; 514/7, 12, 2, 789; 424/417, 450, 460

[56] References Cited

U.S. PATENT DOCUMENTS

| | | | |
|---|---|---|---|
| 5,128,318 | 7/1992 | Levine et al. | 514/2 |
| 5,622,715 | 4/1997 | Barenholz et al. | 424/450 |

OTHER PUBLICATIONS

Szoka et al. (1980) Ann. Rev. Biophys. Bioeng. 9:467–508. Comparative Properties and Methods of Preparation of Lipid Vesicles (Liposomes).

Tall, A.R. (1980) J. Lipid Res. 21:354–363. Studies on the Transfer of Phosphatidylcholine from Unilamellar Vesicles into Plasma High Density Lipoproteins in the Rat.

Mallory et al. (1987) J. Biol. Chem. 262:9, pp. 4241–4247. Expression and Characterization of Human Apolipoprotein A–I in Chinese Hamster Ovary Cells.

Holtfretter et al. (1988) Biol. Chem. Hoppe Seyler. 369:1045–1054.

"Increased Concentrations of Serum Lp(a) Lipoprotein in Patients With Primary Gout"—Annals of the Rheumatic Diseases 1995; 54: 90–93; Takahashi et al.

"Serum Lipoprotein (a) Levels Before and After Subtotal Thyroidectomy in Subjects with Hyperthyroidism"—Metabolism, vol. 44, No. 1 (Jan.), 1995: pp. 4–7; Yamamoto et al.

"Elevated Serum Lp(a) Levels in the Early and Advanced Stages of Breast Cancer"—Cancer Biochem. Biophys., 1994, vol. 14, pp. 133–136; Kokoglu et al.

"Lipoprotein(a) in Type 1 Diabetic Patents with Renal Disease"—Diabetic Medicine (United Kingdom), vol. 11, No. 10, pp. 961–967, 1994 Groop et al.

"Prevention of Restenosis After Percutaneous Transluminal Coronary Angioplasty by Reducing Lipoprotein (a) Levels with Low–Density Lipoprotein Apheresis"—The American Journal of Cardiology, Jun. 1, 1994, vol. 73, No. 15; pp. 1037–1040; Daida et al.

"Uptake of Endogenous Cholesterol by a Synthetic Lipoprotein"—1986 Biochem. Biophys. Res. Commun. 875 = 183–194 (1986); Williams et al.

U.S. application No. 08/257,866, filed Jun. 10, 1994 entitled "Method of Treating Hypertension."

DeLamatre et al. (1986) Biochim. Biophys. Acta, vol. 875, pp. 419–428, 1986.

Davidson et al. (1995) J. Biol. Chem. vol. 270, No. 29, pp. 17106–17113, 1995.

Stein et al. (1975) Biochim. Biophys. Acta, vol. 380, pp. 106–118, 1975.

Holtfreter et al. (1988) Biol. Chem. Hoppe Seyler, 369:1045–1054.

*Primary Examiner*—Robert A. Wax
*Assistant Examiner*—Enrique D. Longton
*Attorney, Agent, or Firm*—Foley & Lardner

[57] ABSTRACT

A lipoprotein particle and a therapeutic lipoprotein composition are disclosed. The lipoprotein particle consists essentially of lecithin phospholipids with low phase transition temperatures and human apoproteins A and C. A therapeutic composition for therapeutic administration to a subject, comprising the lipoprotein particles of the invention, is also disclosed. The composition is useful is treating disease conditions associated with elevated serum Lp(a) levels, as well as hypertension and acute renal failure.

18 Claims, No Drawings

THERAPEUTIC LIPOPROTEIN COMPOSITIONS

FIELD OF THE INVENTION

The present invention relates to a therapeutic lipoprotein composition containing lipoprotein particles formed from small unilamellar vesicles and A and C apoproteins and methods for its formation and use.

REFERENCES

Anselem, S., et al., *LIPOSOME TECHNOLOGY* (Gregoriadis, G., ed), pp. 501–524, CRC Press, Boca Raton, Fla. (1993).

Bailey, J. M., *Exp Cell Res.* 37:175–182 (1965)

Barenholz, Y., et al., *Biochemistry* 16:2806 (1977).

Bisgaier, C. L., et al., *Biochim. Biophys. Acta* 918:242–249 (1987).

Bisgaier, C. L., et al., *J. Biol. Chem.* 264 (2):862–866 (1989).

Blankenhorn, D. H., et al., *J. Am. Med. Assoc.* 257:3233–3240 (1987).

Brissette, L. et al., *J. Biol. Chem.* 261:11631–11638 (1986).

Chung, B. H., et al., *Methods Enzymol.* 128:181–209 (1986).

Daida, H., et al., *Am. J. Cardiol.* 73(15):1037–1040 (1994).

Desmarais, R. L., et al., *Circulation* 91(5):1403–1409 (1995).

Edelstein, C., et al., *J. Biol. Chem.* 247:5842–5849 (1972).

Fiske, C. H., et al., *J. Biol. Chem.* 66:375–400 (1926).

Folch, J., et al., *J. Biol Chem.* 226:497–509 (1957).

Glomset, J. A., *J. Lipid Res.* 9:155–167 (1968).

Haase, A., et al., *Biol Chem Hoppe Seyler*, 369:585–593 (1988).

Harrison, T. R., Ed., *HARRISON'S PRINCIPLES OF INTERNAL MEDICINE, TWELFTH ED.* pp. 839, 1814–1825, McGraw Hill, Inc. (1991).

Hatch, F. T., et al., *Adv. Lipid Res.* 6:1–68 (1968).

Havel, R. J., et al., *J. Clin. Invest.* 34:1345–1353 (1955).

Holmquist, L., et al., *Biochim. Biophys. Acta* 493:400–409 (1977).

Holtfreter, C. et al., *Biol Chem Hoppe Seyler* 369:1045–1054 (1988).

Levida, M. *Handbook of Nutrition in the Aged* (R. R. Watson ed.), CRC Press, pp 89–109 (1985).

Lowry, O. H., et al., *J. Biol. Chem.* 193:265–275 (1951).

Mallory, J. B., et al., *J. Biol. Chem* 262:4241–4247 (1987).

Matz, C. E., et al., *J Biol Chem* 257:4535–4540 (1982).

Miller, G. J., et al., *Lancet* 1:16–19 (1975).

Newman, H. A. I., et al., *J. Lipid Res.* 2: 403–411 (1961).

Noel, S.-P., et al., *Biochim. Biophys. Acta* 754:117–125 (1983).

Rifici, V. A., et al., *Biochim. Biophys. Acta* 834:205–214 (1985).

Shinitsky, M., et al., *J. Biol Chem* 249:2652 (1974).

Szoka, F., et al., *Ann Rev Biophys Bioeng*, 9:467 (1980).

Tenda, K., et al., *Jpn. Circ. J.* 57(8):789–795 (1993).

Yamamoto, K., et al., *Metabolism* 44(1):4–7 (1995).

BACKGROUND OF THE INVENTION

Lipoproteins are high molecular weight particles that are primarily responsible for lipid transport, namely of triglycerides and cholesterol in the form of cholesteryl esters, through the plasma. Five major classes of naturally-occurring lipoproteins are known to circulate in plasma, each differing in lipid composition, apoprotein composition, density, size, and electrophoretic mobility.

Each lipoprotein particle is composed of a non-polar core region, a surrounding phospholipid surface coating containing small amounts of cholesterol, and exposed at the surface, apoproteins responsible for binding to receptors on cell membranes and directing the lipoprotein carrier to its intended site of metabolism.

At least ten different apoprotein molecules have been identified, and each class of lipoprotein particle contains a specific apoprotein (also referred to as apolipoproteins) or combination of apoproteins embedded in its surface (Harrison). These apoproteins are encoded by genes localized to sites on chromosomes 1, 2, 6, 11, and 19, and mutations thereof are thought to play a role in atherogenesis.

The major classes of lipoproteins found in human plasma include chylomicrons and chylomicron remnant particles, VLDL (very low density lipoprotein), IDL (intermediate density lipoprotein), LDL (low density lipoprotein), and HDL (high density lipoprotein).

Chylomicrons contain a hydrophobic core primarily composed of dietary triglycerides and contain several apoproteins including AI, AII, B48, CI, CII, CIII, and E. VLDL contains a core of endogenous triglycerides synthesized in the liver, in addition to apoproteins B48, CI, CII, CIII, and E. IDL particles are composed of lipids including cholesteryl esters and triglycerides and contain apoproteins B100, CIII, and E. A fourth class of lipoprotein, LDL, possesses a core composed almost entirely of cholesteryl esters and has a surface coat containing only apo B100. About three-fourths of the total cholesterol in normal human plasma is contained within LDL particles. A fifth class of lipoprotein, HDL, also contains cholesteryl esters and possesses a surface coating which includes AI and AII apoproteins. A detailed description of the major classes of human lipoproteins and their function in lipid transport is provided in Harrison (Harrison, 1991).

In addition to the major classes of lipoproteins, a lipoprotein-like particle, Lp(a), has been identified and shown to bear a strong resemblance to both lipoprotein and plasminogen. Its protein components include apo B100 linked to apo (a) via a disulfide bridge. Although a relationship has not been clearly established, the structural resemblance of the lipoprotein-like Lp(a) particle to plasminogen is thought to provide a link between lipids, the clotting system, and atherogenesis.

HDL has been shown to be associated with a protective effect against atherosclerosis in humans (Miller, 1975; Blankenhorn, 1987). It has been hypothesized that HDL exerts its protective effect by the reverse transport of excess cholesterol from peripheral tissues to the liver (Bailey, 1965; Glomset, 1968). However, in regard to its role in anti-atherogenesis, the mechanisms of HDL uptake of cholesterol and delivery to the liver remain an issue of debate (Bisgaier, 1988).

In studies in rats, the vast majority of IDL is shown to be rapidly cleared by the liver. The mechanism of IDL uptake is not clearly understood, although it appears to involve a receptor-mediated process (Noel, 1983).

Numerous studies have been undertaken to elucidate the specific mechanisms of lipid uptake by lipoproteins, the role of lipoproteins in atherogenesis, additional physiological roles of lipoproteins, the identification of lipoprotein receptors responsible for cell surface binding, and the like. The findings resulting from such studies are often inconclusive due to the complex nature of lipoproteins and the accompanying complexity of the human lipid transport system, and are often derived from in-vitro studies or are based on animal models.

SUMMARY OF THE INVENTION

The lipoprotein composition contains lipoprotein particles, according to the invention, composed of small unilammellar vesicles of phosphatidylcholine phospholipids, and associated with the phospholipids, are apoproteins from apoprotein classes A and C. The phosphatidylcholine phospholipids have phase transition temperatures between about −10 and 37° C. and are preferably egg phosphatidylcholine phospholipids. The particles form a therapeutic composition for administration to a subject by intravenous administration.

The particles and composition are formed, in one embodiment, by mixing small unilamellar vesicles of phosphatidylcholine phospholipids with a mixture of apoproteins consisting essentially of apoproteins from classes A and C, typically apo A-1 and C class lipoproteins. The components are mixed under conditions effective to form lipoprotein particles in which the apoproteins are vesicle-associated. Typically, the vesicles contained in the composition have sizes between 0.03 and 0.08 microns.

In one general embodiment, the mixing is carried out ex vivo, e.g., by mixing small unilamellar vesicles (SUVs) with a mixture of recombinant A and C apoproteins. In another general embodiment, the mixing is carried out in vivo by administering the SUV's to a human subject, allowing the liposomes to circulate for a period of at least about 2 hours, and then optionally, isolating a serum sample from the subject, and isolating from the serum sample. The lipoprotein particles have a density of between about 1.0006 and 1.019 g/ml.

The particle composition is used, in accordance with another aspect of the invention, for treating a disease state which is responsive to intravenous administration of small unilammelar phosphatidylcholine vesicles, in the dosage range preferably between about 1–50 mg vesicle lipid/kg subject body weight. The treatment method includes administering to a subject in need of such treatment, a therapeutically effective dose of a lipoprotein composition, and repeating the administering, if necessary, until a measurable improvement in the disease state is observed.

In one embodiment the method is used in treating acute renal failure in a subject, as evidenced by a ratio of urine-to-plasma creatinine less than about 20, where the composition is administered until a significant increase in urine-to serum creatinine ratio is achieved.

In another aspect, the method is used in treating hypertension in a subject having elevated diastolic blood pressure, where the composition is administered until a significant reduction in blood pressure, e.g., a 20% reduction in diastolic blood pressure, is achieved.

In a related aspect, the invention includes a method of treating a disease state which is associated with elevated levels of Lp(a), by administering to a subject having an elevated serum Lp(a) level, a therapeutically effective dose of the lipoprotein composition, with repeated administration, if necessary, until a measurable reduction in serum Lp(a) level is observed.

These and other objects and features of the invention will become more fully apparent when the following detailed description is read in conjunction with the accompanying figures and examples.

DETAILED DESCRIPTION OF THE INVENTION

I. Definitions

Unless indicated otherwise, the terms below have the following meanings:

"Empty" liposomes refers to liposomes that do not contain entrapped or encapsulated drug.

"Recombinant apoprotein" refers to an apoprotein which is prepared by genetic engineering techniques commonly known in the art. Recombinant apoproteins are produced typically by cloning the gene of interest into a vector for introduction into any of a number of expression systems such as $E.\ coli$, yeast, cultured mammalian cells, and the like.

Small unilammelar vesicles (SUVs) refer to small single-bilayer liposomes having sizes between about 0.02 to 0.12 microns, preferably 0.02 to 0.08 microns.

"Associated apoproteins" in the context of the present invention refers to apoproteins which are stably bound to the SUV's, as evidenced by the ability of SUV's and associated apoproteins to co-migrate in density centrifugation.

A "significant improvement" in a disease state is a measurable degree of improvement, as indicated by either a clinical or biochemical indicator, in the disease state. Typically, a significant improvement in a disease state is one which results in an improvement of a parameter with a known correlation to the disease state of at least five percent. For example, with respect to conditions associated with elevated serum LP(a) levels:

The term elevated Lp(a) concentration refers to a serum Lp(a) concentration above 25 mg/dl. The term chronic elevated Lp(a) concentration, as used herein, refers to a concentration of Lp(a) that is on average elevated above normal average serum Lp(a) concentrations when measured at various times over the course of a week. A normal average serum Lp(a) concentration is generally below 25 mg/dl.

The term significant reduction in Lp(a) concentration, as used herein, refers to a reduction of at least 20%, preferably more than 40%, with respect to the pretreatment Lp(a) concentration in a subject.

In the case of elevated blood pressure, a significant reduction in blood pressure is a reduction of at least about 10% in diastolic pressure.

II. Preparation of Lipoprotein Composition

The present invention involves, in one aspect, a therapeutic lipoprotein composition for use in intravenous administration to a subject. The lipoprotein composition contains lipoprotein particles of the invention composed of small unilammelar vesicles (SUVs) having associated A and C apoproteins. Preparation of the lipoprotein particles of the present invention is described in the Examples and in the sections which follow.

A. Preparation of Liposomes: Composition

The lipoprotein particles of the present invention are composed of small unilammelar vesicles. In one preferred embodiment, described and used in the examples below, the liposomes are composed predominantly (more than 50 mole percent, preferably more than 80–90 mole percent) of phosphatidylcholine (PC) having a phase transition temperature less than about 37° C., preferably between about −10 to 24° C., e.g., about 5° C. or less.

The lipoprotein composition used in the method of the present invention is composed primarily of PC phospholipids. PC phospholipids include those phospholipids having a choline moiety and where the fatty acid chain portion of the phospholipid may vary in length and degree of unsaturation.

One preferred vesicle composition includes egg PC, which has a transition temperature of −5° C., and contains predominantly 1-palmitoyl, 2-oleyl PC and 1-palmitoyl,2-linoleyl PC. Alternately, phosphatidylcholine may be isolated from rat liver (Newman, 1961), followed by purification on alumina (Shinitzky, 1974).

The liposomes may be composed entirely of egg PC, or may contain other lipid components which (i) are not immunogenic, (ii) do not contribute a significant portion, i.e., more than 25–50 mole percent, of lipids with high phase transition temperature. Additional components may include negatively charged lipids, such as phosphatidylglycerol (PG) or phosphatidylserine (PS). Of course, the mole percentage of these lipids should be relatively low with respect to PC. The liposomes may also include cholesterol or other sterols, in an amount preferably less than about 40 mole percent.

Lipid protective agents, such as α-tocopherol, α-tocopherol acetate, or α-tocopherol succinate, may also be included in the lipids forming the liposomes, to protect the lipid components against free radical damage (Levida). Typically such agents are included at a mole percentage between about 0.5% and 2%. It is advantageous to add α-tocopherol to the liposomes to maintain a balance between vitamin E and polyunsaturated lipids in the liposomes.

B. Preparation of Unsized Liposomes

A variety of methods for producing liposomes are available, and these have been extensively reviewed (Szoka 1980). In general these methods produce liposomes with heterogeneous sizes from about 0.02 to 10 microns or greater. As will be discussed below, liposomes which are relatively small and well-defined in size are preferred for use in the present invention, hence a second processing step for reducing the size and size heterogeneity of liposomal suspensions will usually be required.

In one preferred method for forming the initial liposome suspension as described in Example 1, the vesicle-forming lipids are taken up in a suitable organic solvent system, preferably in a siliconized glass vessel, and dried in vacuo or under an inert gas to form a lipid film. An aqueous suspension medium, such as a sterile saline solution, is added to the film, and the vessel is agitated (e.g., on a shaker or using a sonicator) until the lipids have hydrated to completion, typically within about 1–2 hours. The amount of aqueous medium added is sufficient to produce a final liposome suspension containing preferably between about 10 and 30 g lipid per 100 ml media.

During the hydration stage, the lipids hydrate to form multilamellar vesicles (MLVs) with sizes ranging between about 0.5 microns to about 10 microns or larger. In general, the size distribution of MLVs can be shifted toward slightly smaller sizes by hydrating the lipids under more vigorous agitation conditions.

Example 1 describes the preparation of egg PC MLVs, followed by treatment of the MLVs with ultrasonic irradiation to reduce the liposome sizes to produce the desired SUVs. Sizing methods for producing SUVs from larger multilamellar vesicles are described in further detail below.

The aqueous medium used in forming the liposomes may contain water-soluble agent(s) which enhance the stability of the liposomes upon storage. A preferred stabilizing agent is an iron-specific trihydroxamine chelating agent, such as desferrioxamine. The use of this compound in reducing lipid peroxidation and free radical damage in drug-containing liposomes has been reported in U.S. Pat. No. 4,797,285. Briefly, it was shown that the combination of a lipophilic free-radical quencher, such as α-tocopherol, and the water-soluble chelator gave substantially better protection against lipid peroxidation damage than did either of the protective agents alone. The chelator is included in the aqueous medium in molar excess of the amount of free iron in the medium. Typically, a chelator concentration of between about 10–200 micromolar is sufficient for reducing lipid peroxidation and free radical damage.

C. Sizing Liposomes: SUV Preparation

The suspension of liposomes prepared as described above is preferably further treated to produce liposomes having a desired size and size homogeneity.

The liposome suspension is generally sized to achieve a selective size distribution of vesicles in a size range less than about 1 micron and preferably less than about 0.8 microns. Liposomes in this size range can be readily sterilized by filtration through a depth filter. Smaller vesicles also show less tendency to aggregate on storage, thus reducing the potential for serious vascular blockage problems upon intravenous administration of the final lipoprotein composition of the present invention. Finally, liposomes which have been sized down to the submicron range possess more uniform biodistribution and drug clearance characteristics.

Preferred liposomes are small unilamellar vesicles (SUVs), i.e., single-bilayer liposomes having sizes between about 0.02 to 0.08 microns. SUVs have been shown to possess relatively long blood circulation halflives, when administered intravenously, as described in co-owned U.S. patent application Ser. No. 08/257,899, filed on Jun. 10, 1994. Briefly, as described therein, plots of liposome retention in the bloodstream, measured up to 1,000 minutes after IV injection, revealed that significant quantities of liposomes remained in the bloodstream even at 1,000 minutes.

Several techniques are available for reducing the sizes and size heterogeneity of liposomes, in a manner suitable for preparing the small unilammelar vesicles of the present invention. Ultrasonic irradiation of a liposome suspension either by bath or probe sonication produces a progressive size reduction down to SUVs. A sonicating procedure used to produce SUVs is described in Example 1.

Homogenization is another method which relies on shearing energy to fragment large liposomes into smaller ones. In a typical homogenization procedure, MLVs are recirculated through a standard emulsion homogenizer until selected liposome sizes, typically less than 0.1 microns, are observed.

Extrusion of liposomes through a small-pore polycarbonate membrane is an effective method of reducing liposome size down to a relatively well-defined size distribution. An average range is between about 0.03 and 1 micron, depending on the pore size of the membrane, such as described in Example 2. Typically, the suspension is cycled through the membrane several times until the desired liposome size distribution is achieved. The liposomes may be extruded through successively smaller pore membranes, to achieve a gradual reduction in liposome size.

Liposome particle sizes can be determined by a number of techniques including electron microscopy, comparative chromatography (Bisgaier, 1989) and quasi-elastic light scattering.

The size-processed liposome suspension may be readily sterilized by passage through a sterilizing membrane having a particle discrimination size of about 0.2 microns, such as a conventional 0.22 micron depth membrane filter. If desired, the liposome suspension can be lyophilized for storage and reconstituted shortly before use.

D. Apoprotein Components

The lipoprotein composition of the present invention contains lipoprotein particles of the invention which are composed of SUVs as described above, and associated with the SUVs, are molecules of serum proteins, namely human apoproteins. Based upon the applicants' identification of a new lipoprotein fraction isolated from blood samples withdrawn from subjects post-SUV infusion, preferred apoproteins are class A and C apoproteins, and particularly apo A-1 and apo Cs.

Apoproteins, a component of naturally-occurring lipoproteins, may be recovered from samples of the corresponding lipoprotein containing such apoprotein(s), typically derived from either human or rat. In an exemplary procedure, the desired lipoprotein fraction is first isolated from plasma by ultracentrifugation (Hatch, 1968; Chung, 1986) using an appropriate density gradient, followed by purification, typically dialysis.

Typical sources for the A and C apoproteins are HDL and VLDL, although any lipoprotein containing A and C apoproteins is suitable. Generally, high density lipoproteins are isolated by ultracentrifugation at densities from 1.063–1.21 g/ml (Havel, 1955), followed by washing by reflotation at a density of 1.21 g/ml.

Isolation of $HDL_3$, one potential source of apo A-1, has also been described (Brissette, 1986). Briefly, human $HDL_3$ is prepared by sequential ultracentrifugations between densities 1.125 and 1.21 g/ml and isolated at density 1.21 g/ml ($4.6 \times 10^6$ g/h). The $HDL_3$ is then washed under similar conditions, followed by dialysis against a saline solution containing EDTA and sodium azide.

VLDL, from either rat serum or human plasma, is similarly isolated using ultracentrifugation with an appropriate density gradient. In a typical procedure, VLDL is isolated from human plasma by ultracentrifugation at $8.5 \times 10^4$ g for about 0.5 h to remove chylomicrons, followed by two rounds of ultracentrifugation at $1.8 \times 10^6$ g/h to isolate and wash the VLDL (Brissette, 1986).

Isolation of apoproteins from the corresponding lipoprotein fraction can be carried out by a number of suitable techniques. Both apo A-I and A-IV can be recovered from HDL. In one such method, apo A-1 and A-IV are isolated from HDL by gel filtration and ion-exchange chromatography (Edelstein, 1972; Rifici, 1985). Apo A-1 may also be extracted from a solution of human $HDL_3$ by precipitation with acetone, followed by centrifugation (Brissette, 1986). In a similar fashion, apo E and apo Cs can be isolated from VLDL using selective extraction procedures (Holmquist, 1977).

Generally, isolated apoprotein fractions are identified by either immunodiffusion analysis with antibodies against the target apoprotein(s) (Bisgaier, 1987) or by polyacrylamide gel electrophoresis. A suitable gel system for carrying out electrophoretic analysis is 4–18% polyacrylamide gradient gel in the presence of sodium dodecyl sulfate and β-mercaptoethanol.

A typical polyacrylamide gel electrophoretic mobility pattern for a mixture containing apo E, apo A-I, apo A-II, apo Cs and apo Bs reveals a progression, taken from the origin, as follows: apo Cs and A-II, apo A-I, apo E, apo $B_1$ and apo $B_h$, as provided in Brissette (Brissette, 1986).

In some instances, the isolated apolipoproteins may optionally contain a radiolabel such as iodine-125. Radiolabelled apoproteins may be useful in initial experiments for forming the lipoprotein particles of the present invention by providing a means for estimating the level of apoprotein-Suv association.

Alternatively, apoproteins for use in the present invention may be formed recombinantly. Expression of apoprotein genes is known in the art. Human apo C-II can be prepared by cloning a full length human apo C-II cDNA insert into the pSP19 expression vector, followed by transcription and translation in vitro (Holtfreter, 1988). Mature apo CII can be expressed in E. coli transformed with the pKK233-2 apo CII clone, or alternatively, can be formed on a preparative scale by integrating apo CII cDNA into the pUR291 vector (Holtfreter, 1988).

Expression of human apo A-I and apo A-II genes in Xenopus laevis ooctyes has also been described (Haase, 1988). In following the method of Haase, apo A-I and apo A-II genes can be isolated as clones and transcribed and translated in Xenopus laevis oocytes. Simultaneous injection of the apo A-I and apo A-II genes leads to secretion of both apoproteins, which may then be separated by density gradient centrifugation as has been described. Apo A-1 can also be produced in Chinese hamster ovary (CHO) cells by transfection of the CHO cells with an expression plasmid which places the human apo A-I gene under the direction of the human metallothionein II gene promoter (Mallory, 1987).

E. Forming the Lipoprotein Composition

IN VITRO METHOD:

The therapeutic lipoprotein composition provided by the present invention contains lipoprotein particles of the invention composed of small unilamellar vesicles of phosphatidylcholine phospholipids having associated A and C apoproteins. The lipoprotein particles of the present invention may be prepared by both in-vitro and in-vivo methods, as will herein be described.

In accordance with one method of the invention, the lipoprotein particles are formed by mixing phosphatidylcholine SUVs with apoproteins under conditions suitable for forming apoprotein-associated SUVs. In one such exemplary approach, PC liposomes prepared as described above are incubated with apoprotein. Typically, apoprotein is incubated with the SUVs for a period of at least 1 hour and preferably for 4–8 hours, at temperatures between about 25° C.–37° C. To determine the appropriate concentration of apoprotein, the incubation is typically performed at several different concentrations of protein and the degree of association is determined, based upon the amount of free apoprotein remaining. For each apoprotein contained in the mixture, the protein/phospholipid ratio will typically range from about 0.1–1 (on a μg-to μg basis), with concentrations of SUVs and protein contained in the mixture between about 10–80 μg/ml.

Apoproteins for use in forming the lipoprotein particles of the present invention include apo As (primarily apo A-1, apo A-II, apo A-IV) and apo Cs (primarily apo C-I, apo C-II, apo C-III). In one embodiment, the lipoprotein particles contain apo A-I and apo Cs. The apoproteins may be derived from extracted lipoprotein sources or may be recombinant apoproteins, as described above.

Returning to preparation of the lipoprotein particles, excess or non-associated apoprotein is removed from the mixture, typically by washing followed by centrifugation. Following verification of purity, the resulting suspension of lipoprotein particles may be stored as a suspension, or alternatively, the lipoprotein particles may be isolated.

Isolation of the newly formed lipoprotein particles is carried out using a Ficoll gradient flotation protocol. In one such exemplary isolation method, the lipoprotein particles are mixed with a Ficoll solution in phosphate-buffered saline and placed in a centrifuge tube. The solution is then overlayed with Ficoll, followed by a layer of phosphate-buffered saline. The resulting mixture is then centrifuged. Lipoprotein particles floated to the saline and Ficoll layers are collected and the procedure is repeated. The recovered liposomes may be analyzed by SDS-PAGE, typically carried out on acrylamide gel under reducing conditions. Based upon analysis of the resulting electrophoretic patterns, the lipoprotein particles of the present invention are identified by a distinct band having an electrophoretic mobility and density distinct from those of the reaction components and from naturally-occurring lipoproteins. The lipoprotein particles of the present invention are characterized by densities between those of VLDL and LDL, namely between 1.0006 and 1.019 g/ml. The ratio of protein/phospholipid (m/m) in the isolated lipoprotein fraction will generally be between about 0.05–0.5 for each of the apoproteins present.

Protein levels in the recovered lipoprotein particles can be verified using the method of Lowry (Lowry, 1951). Phospholipid concentrations can be determined as described in Example 5 or by digestion with perchloric acid to promote phosphate cleavage (Fiske, 1926).

In an alternate embodiment, the lipoprotein particles are formed by incorporating apoprotein directly during SUV preparation. In this approach, SUVs are prepared and sized as described in Examples 1 and 2, with the exception that apoprotein is included with the vesicle-forming lipids used to form the initial lipid film. Protein is added at a protein/phospholipid (mass/mass) ratio typically between about 0.1–1.

Alternately, the cholate-lipid dispersion method can be used to complex purified A and C apoproteins to egg PC liposomes containing cholesterol (Matz, 1982).

IN VIVO METHOD:

In accordance with another aspect of the present invention, the lipoprotein particles of the invention are formed by intravenously administering small unilamellar vesicles to a subject, allowing the liposomes to circulate in the bloodstream, and optionally isolating from a blood sample withdrawn from the subject, the lipoprotein particles of the invention.

Preparation of lipoprotein particles according to this aspect of the invention is supported in Examples 3 and 6, and will be further described below.

In this approach, small unilamellar vesicles composed of phosphatidylcholine, as described in Examples 1 and 2 and sections IIA-C herein, are intravenously administered to an animal or human subject. The vesicles may be administered in a single dose, or in multiple doses. The amount of liposomes administered at each dose is between about 10 and 1000 mg lipid per kg of body weight, and preferably between about 50–1000 mg lipid per kg of body weight. After allowing the injected liposomes to circulate in the bloodstream for a period of several hours, preferably at least 2 hours, e.g., 6–24 hours, a blood sample is removed from the subject. The lipoprotein particles of the present invention may be isolated from serum and used as described above. The lipoprotein particles form in the bloodstream.

The post-infusion lipoprotein particles are typically separated from naturally occurring lipoproteins by ultracentrifugation, the method of which has been previously described herein. The lipoprotein particles are purified by gel electrophoresis, typically using a gradient of polyacrylamide. The lipoprotein particles of the invention, as formed by intravenous administration of PC SUVS, are characterized by a density between that of VLDL and LDL, namely between about 1.0006 and 1.019 g/ml.

III. Methods of Treating Disease States

This section describes treatment methods which involve intravenous administration of the lipoprotein particle composition described above. In all of these methods, the composition is administered intravenously at in a dose and dosing frequency effective to produce a desired improvement in the treated condition.

A preferred dosing frequency is one-two times per week. The dosing periods, e.g., two weeks, may be interrupted by a wash-out period, typically of 1–4 weeks. The treatment, e.g., involving repeating dosing and wash-out periods, may continue over an extended period of several months or more.

The amount of composition administered at each dose is preferably between about 1 to 50 mg vesicle lipid per kg of body weight. In a preferred embodiment, the liposome suspension is administered one time per week, at a dose of about 5–20 mg lipid/kg body weight.

A typical dose for an 80 kg individual would be between about 0.4 to 1.6 grams lipid, corresponding to between 2–8 ml of a particle suspension containing 200 ms lipid/ml. Administration may be by iv (intravenous) injection, or iv drip (infusion). The particle composition may be suspended in sterile saline or in a nutritional or drug-containing buffer or medium, such as a glucose/salt medium, to combine liposome treatment with other parenteral therapy.

A. Treatment of SUV-Responsive Disease States

The applicants have previously demonstrated the ability to treat a number of disease conditions, including acute renal failure and hypertension, by intravenous infusion of SUV's of the type employed in the preparation of the present particle composition.

In the present invention, these conditions and disease states are treated by intravenous administration of the serum particles like those formed with IV administration of such SUV's, as demonstrated above. The advantage of the present invention over IV administration of precursor SUV's is threefold:

First, the apoprotein particles can be expected to form in vivo only after a several hour period, and thus a substantial percentage of administered SUV's is cleared before effective apolipoprotein particle formation occurs. Thus, substantially less liposome lipid is required in the present invention, where the particles are active immediately on administration.

Secondly, the activity of the lipoprotein particles formed in vivo is limited by the amount of serum apoprotein available for binding to the administered liposomes. The present composition can be produced with relatively high concentrations of apoproteins, permitting therapeutic effectiveness at significantly lower amounts of administered liposomal lipid.

Finally, the composition of the invention does not rely on depleting existing serum apoproteins A and C, either in free or HDL form, from the bloodstream, so that the administered liposome/apoprotein particles tend more to augment, rather than replace, native HDL particles.

In one embodiment, the method is employed for use in treating acute renal failure (ARF) in a subject, as evidenced by elevated levels of serum creatinine. ARF is typically detected by determination of glomerular filtration rate (GFR) or blood urea nitrogen or serum creatinine levels.

GFR is the rate of ultrafiltration of plasma across the walls of the glomerular capillaries and measurement of total GFR of both kidneys provides a sensitive index of overall renal excretory function. Normal renal excretory function is indicated by a GFR of about 125 mL/min (180 L/day), although when renal excretory capacity is impaired, total GFR declines.

Often, measurements of urea and creatinine concentrations are used to assess the glomerular filtration rate. Both substances are produced at a relatively constant rate by the liver and muscles; an increase in their respective serum concentrations occurs as GFR declines due to the fact that both compounds undergo complete glomerular filtration and are not reabsorbed by the renal tubules. Creatinine provides a more reliable index of GFR than urea because urea can back diffuse more completely from tubule lumen to peritubular blood than creatinine.

Chemical analysis of both urine and serum samples are useful indicators of ARF. For example, the range of urine osmolalities that can be achieved by an individual with normal-functioning kidneys (40 to 1200 mosmol/kg) is much larger than the range achievable in diseased kidneys (250–350 mosmol/kg). Typically, acute renal failure is characterized by urine osmolalities of below about 400 mosmol/kg, urine sodium concentrations above about 40 mmol/L, a ratio of urine-to-plasma creatinine levels below 20, and a fractional excretion of filtered sodium, defined as the ratio of urine sodium concentration/serum sodium concentration to urine creatinine concentration/serum creatinine concentration multiplied by 100, of about 2 (Harrison).

In the present embodiment, a person having acute renal failure, as evidenced by a ratio of urine-to-plasma creatinine levels less than about 20, is treated by iv administration of the lipoprotein composition of the invention, as described above. The therapeutic effect of the treatment is monitored by assaying urine-to-serum creatinine levels (or other characteristic of ARF discussed above). Treatment is continued, i.e., with repeated administration 1–2 times/week, until a significant improvement (rise) in urine-to-serum creatinine level is achieved.

In another embodiment, the method is employed for the treatment of hypertension. Hypertension refers to elevated arterial pressure, and is typically reported as a ratio of systolic pressure (arterial pressure during contraction of the heart muscle) to diastolic pressure (residual arterial pressure during relaxation of the heart muscle), reported in units of mm Hg. A normal diastolic blood pressure is between about 60–85 mm Hg. Diastolic pressures above 85 mm Hg are generally diagnostic of hypertension.

In the present invention, a subject having elevated blood pressure, i.e., diastolic pressure above about 85 mm Hg, is treated by iv administration of the lipoprotein particles of the invention. Therapeutic effectiveness is followed by monitoring blood pressure, preferably diastolic blood pressure. Treatment is continued until, e.g., by repeated administration of the composition 1–2 times/week, until a significant reduction, and preferably at least a 10% reduction in diastolic blood pressure is observed.

B. Treatment of Disease States Associated with Elevated Lp(a)

In another general embodiment, the invention provides a method of reducing the serum Lp(a) concentration in a person at risk for developing a disease condition associated with a chronic elevated serum Lp(a) concentration. Conditions associated with elevated Lp(a) concentrations include, for example, gout, breast cancer and hyperthyroidism.

A chronically elevated Lp(a) concentration refers to a serum Lp(a) concentration that is above about 25 mg/dl, typically representing an average of Lp(a) values, when measured several times over the course of a week. Serum Lp(a) concentrations can be measured by a variety of methods, including enzyme-linked immunoabsorbent assay (ELISA), latex immunoassay or immunoradiometric assay. A specific kit for determining Lp(a) concentration in a blood sample, Macra™, is available from Terumo diagnostics (Elkin, Md.).

In the present invention, a subject having elevated Lp(a) level, i.e., a serum Lp(a) level above 25 mg/dl, Hg, is treated by iv administration of the lipoprotein particles of the invention. Therapeutic effectiveness is followed by monitoring serum Lp(a) level, and treatment is continued until, e.g., by repeated administration of the composition 1–2 times/week, until a significant reduction, and preferably at least a 20–40% reduction in serum Lp(a) level is observed.

In more specific embodiments, the invention includes a method of treating gout, breast cancer or hyperthyroidism in a subject having one of these conditions and an elevated serum Lp(a) concentration. Studies have shown that serum Lp(a) concentrations are elevated in many subjects with gout (Takahashi), various types of cancer, such as breast cancer (Kokoglu), and hyperthyroidism (Yamamoto). The purpose of this method is to treat the clinical disease by lowering Lp(a) levels, as one of the underlying factors contributing to the disease.

Treatment, in accordance with the method of the invention, involves first determining serum Lp(a) concentration in a person having one of the above clinical conditions. A patient having an elevated Lp(a) level is then selected as a candidate for the liposome treatment method, as described above, typically as an adjunct to another treatment method, such as surgery, chemotherapy, or radiation therapy in the case of breast cancer. Treatment is maintained until a significant reduction in Lp(a) is observed and preferably throughout the treatment period for the clinical disease.

C. Treatment of Restenosis

Restenosis occurs in approximately 20–30 percent of patients following percutaneous transluminal coronary angioplasty. Restenosis can also occur in patients following surgical resectioning of vascular tissue. In this procedure, a region of stenosis in a vessel is removed and the vessel is sutured closed. Restenosis in each case is apparently the result of excessive local myointimal hyperplasia, brought about by platelet aggregation to the freshly dilated or sutured vessel surface (Harrison).

Recent studies have shown that high serum Lp(a) concentrations are associated with an increased incidence of restenosis after balloon angioplasty (Daida, Desmarais, Tenda). In one study, patients with a serum Lp(a) level of 38 mg/dl had a significantly higher level of restenosis than patients with a serum level of 19.9 mg/dl (Tenda).

The present invention includes a method of reducing the extent of restenosis following procedures such as balloon angioplasty or surgical resectioning of vascular tissue. Typically in the method, a person undergoing such a procedure that can lead to restenosis is given one or more pretreatment administrations of the lipoprotein particle composition, particularly where existing Lp(a) levels are elevated, to achieve a reduction in such levels. Following the procedure, the patient is again monitored for Lp(a) serum concentrations, and given further particle injections if necessary to maintain or achieve low Lp(a) levels, e.g., 20 mg/dl or lower. The treatment may be discontinued after a period of several weeks or more when the risk of restenosis has passed.

The following examples illustrate, but in no way are intended to limit the scope of the present invention.

MATERIALS AND METHODS

Egg phosphatidylcholine (egg PC) recovered from egg yolk may be prepared according to known methods (Shinitsky, et al., 1974). High purity egg PC may also be purchased from Avanti Polar Lipids (Alabaster, Ala.), Lipoid KG (Ludwigshafen, Germany), or from Sigma (St. Louis, Mo.). The egg PC used to form small unilamellar vesicles as described below was determined to be greater than 99% pure by thin layer chromatography (TLC) analysis.

EXAMPLE 1

PREPARATION OF SMALL UNILAMELLAR VESICLES: SONICATION

Egg PC dissolved in chloroform was placed in a 100 ml vessel and dried to a thin film under an inert atmosphere of nitrogen. Sterile saline was added to the lipid film to a final concentration of about 100 mg/ml, and the lipid film was hydrated with swirling. The resulting multilamellar vesicle (MLV) suspension was then bath sonicated for 1 hour using a Heat System Sonicator, Model 375W, at a power setting of 40–50% full value. The temperature of the suspension was maintained at about 4° C. during sonication. Large vesicles or MLVs were separated from the sonicated suspension by ultracentrifugation at 100,000 g for 1 hour (Barenholz, 1977). The remaining suspension of SUVs, having a concentration of about 100 mg/ml, was then filter sterilized.

EXAMPLE 2

PREPARATION OF SMALL UNILAMELLAR VESICLES: EXTRUSION

Homogeneous small unilamellar vesicles of egg PC with an average diameter of 39±8 nm, in 0.15 M NaCl were prepared by extrusion using serial filtration through polycarbonate filters in a GH 76-400 pressure cell (Nucleopore) (Anselem, et al., 1993). Liposomal size was determined using a Coulter model N4 sub-micron particle analyzer equipped with a size distribution processor analyzer (Barenholz, et al., 1993). The final extrusion step was through a 0.05 micrometer pore polycarbonate filter. Egg PC SUV's were sterilized by filtration through sterile 0.22 micrometer Millipore filters.

EXAMPLE 3

EFFECTS OF EGG SUV PC TREATMENT ON THREE MALE SUBJECTS

Suspensions of small unilamellar vesicles prepared as described in Examples 1 and 2 above were administered over a 7 week period to three subjects.

TABLE I

| Subject No. | Gender | Age |
|---|---|---|
| (1) | male | 40 |
| (2) | male | 54 |
| (3) | male | 64 |

The following treatments were administered to each of the three subjects:

TABLE II

| Treatment No. | Week | Treatment Regime |
|---|---|---|
| 1 | 1 | i.v. infusion of 250 ml of 0.9% NaCl solution, followed by i.v. infusion of 200 mg SUVs/kg body weight |
| 2 | 2 | i.v. infusion of 300 mg SUVs/kg body weight |
| 3 | 3 | i.v. infusion of 300 mg SUVs/kg body weight |
| 4 | 4 | i.v. infusion of 300 mg SUVs/kg body weight |
| — | 5–8 | i.v. administration suspended |
| 5 | 9 | treatment resumed with i.v. infusion of 300 mg SUVs/kg body weight |
| 6 | 10 | i.v. infusion of 300 mg SUVs/kg body weight |
| 7 | 11 | i.v. infusion of 300 mg/kg SUV/kg body weight |

Over the course of treatment, pulse rate, blood pressure, body temperature and body weight were monitored and no significant changes were observed.

None of the subjects reported hypersensitivity reaction or other adverse effects relating to SUV treatment.

Subject No. (1) reported an improvement in skin texture, noting that his skin appeared to be more "silky". Subject No. (3) reported an improvement in his ability to perform strenuous physical activity and in the condition of his gums.

Laboratory test results for each of the subjects revealed no abnormalities in liver function, renal function, glucose, electrolytes, CPK and aldolase levels. Complete blood count, coagulation tests and blood hormone levels (e.g., thyroid stimulating hormone (TSH), cortisol and testosterone) were within normal ranges and did not change significantly over the course of treatment. EKG traces for each of the subjects were normal over the course of treatment and abdominal ultrasound performed before and after completion of the study were normal and revealed no indications of fatty liver.

EXAMPLE 4

OSMOTIC FRAGILITY OF RED BLOOD CELLS

The osmotic fragility of red blood cells from each of subjects (1)–(3) was determined over the period of SUV treatment.

Hypotonic solutions of sodium chloride at pH 7.4 were used to determine the concentration at which cell lysis occurred for both fresh red blood cells and for red blood cells which were incubated for 24 hours at 37° C. The concentration of sodium chloride at which lysis occurred in 50% of the cells (e.g., the median corpuscular fragility or MCF) was used as an indication of cell osmotic fragility.

Red blood cell samples (both pre and post infusion) exhibited MCF values at 20° C. and pH 7.4 within a concentration range of 4.0–4.5 g NaCl/ml for fresh red blood cells and between 4.65–5.9 g NaCl/ml for red blood cells incubated at pH 7.4 at a temperature of 37° C. for 24 hours.

The MCF values for all samples remained in the normal range over the course of the study.

EXAMPLE 5

RATE OF APPEARANCE AND CLEARANCE OF SUVs IN THE CIRCULATION

Serum phospholipid levels were determined in order to follow the rate of appearance and clearance of intravenously administered liposomes in the circulation.

Serum isolated from blood samples taken from each of the subjects at various times after SUV infusion were extracted by standard methods.

Phosphatidylcholine concentrations in blood following liposome injection were determined by measuring the increase in inorganic phosphate ($P_i$) in serum. PC concentrations determined based upon determination of inorganic phosphate were confirmed by an enzymatic assay specific for choline phospholipids.

PC levels in serum reached maximal levels at the end of the infusion period, decreased considerably over the next 24 hours following infusion and gradually increased to preinfusion values at day 8. Based upon this finding, the treatment regime described in Table 2 (e.g., infusion every 7 days) was followed.

EXAMPLE 6

ISOLATION AND CHARACTERIZATION OF LIPOPROTEIN PARTICLES

Liposomes were recovered from blood samples withdrawn from the patients at various times after infusion and isolated by centrifugation at a density of 1.006 g/ml or 1.019 g/ml. The recovered post-infusion liposomes were characterized as a distinct lipoprotein fraction just above LDL.

The post-infusion liposomes in the isolated lipoprotein fraction were then examined by electron microscopy and observed to form bilayers. Electron micrographs of negatively stained LDL and VLDL fractions revealed that both the LDL and VLDL fractions also contained liposomes.

The composition of the recovered lipoprotein fraction was determined by SDS-PAGE on acrylamide gel. Based upon electrophoretic mobility, the isolated lipoprotein fraction was determined to contain Apo A-1, Apo E, and Apo Cs. Apo B was not detected. The recovered lipoprotein fraction was also found to contain free cholesterol. The composition and characteristics of the recovered lipoprotein fraction are summarized in Table III below.

TABLE III

New Lipoprotein Fraction

| | |
|---|---|
| Density (g/ml) | between 1.006–1.019 |
| Electron micorscopy | bilayers |
| | size estimate? |
| Apoproteins: | Apo A-1 |
| | Apo Cs |
| | Apo E |
| Lipids | phospholipid |
| | free cholesterol |

EXAMPLE 7

POST SUV TREATMENT: PLASMA ANALYSIS

Plasma isolated from blood samples taken from each of the subjects at various times after SUV infusion was analyzed for free cholesterol content, levels of LDL-C, HDL-C, Apo A-1, triglycerides, and Lp(a).

Twenty four hours after infusion with SUVs, red blood cell free cholesterol levels were found to be reduced by 27%, 10.5% and 18% in subjects No. (1), (2), and (3), respectively, and returned to baseline values 24 hours later. The change in red blood cell cholesterol content following SUV infusion did not affect red blood cell osmotic fragility. No signs of homolysis were observed, as indicated by constant levels of serum haptoglobin and free hemoglobin observed both before and after SUV treatment.

Post SUV infusion serum samples were centrifuged at a density of 1.019 g/ml to isolate the LDL-C fraction. No significant change in the post-infusion LDL-C fraction was observed.

Plasma analysis also revealed that during the course of treatment, profiles of HDL-C and apo A-1 levels tended to rise. Triglyceride levels remained substantially unchanged. Lp(a) levels were found to be substantially reduced. Levels of free cholesterol in plasma were found to increase after Suv infusion, and returned to baseline levels as the liposomes were cleared through the circulation.

TABLE IV

Post SUV Treatment: Plasma Analysis Summary

| Free cholesterol | LDL-C | HDL-C | Apo A-1 | Triglycerides | Lp(a) |
|---|---|---|---|---|---|
| increased | no change | increased | increased | no change | reduced |

While the invention has been described with reference to specific methods and embodiments, it will be appreciated that various modifications and changes may be made without departing from the invention.

It is claimed:

1. A therapeutic lipoprotein composition for intravenous administration to a subject, prepared by: mixing small unilamellar vesicles composed of phosphatidylcholine phospholipids having phase transition temperatures between about −10° and 37° C. with a mixture of apoproteins consisting essentially of apoproteins from classes A and C, under conditions effective to form lipoprotein particles composed of said vesicles and associated A and C apoproteins.

2. The composition of claim 1, wherein the vesicles are empty vesicles.

3. A therapeutic lipoprotein composition for intravenous administration to a subject, prepared by: mixing small unilamellar vesicles composed of phosphatidylcholine phospholipids having phase transition temperatures between about −10° and 37° C. with a mixture of apoproteins consisting essentially of apoproteins from classes A and C, under conditions effective to form lipoprotein particles composed of said vesicles and associated A and C apoproteins, wherein the vesicles have sizes between 0.02 and 0.08 microns.

4. The composition of claim 1, wherein the vesicles are composed of egg phosphatidylcholine.

5. The composition of claim 1, wherein the apoproteins include apo A-1 and class C apoproteins.

6. The composition of claim 5, wherein the apoproteins are human recombinant apoproteins.

7. A therapeutic lipoprotein composition for intravenous administration to a subject, prepared by: mixing small unilamellar vesicles composed of phosphatidylcholine phospholipids having phase transition temperatures between about −10° and 37° C. with a mixture of apoproteins consisting essentially of apoproteins from classes A and C, under conditions effective to form lipoprotein particles composed of said vesicles and associated A and C apoproteins, wherein the lipoprotein particles are characterized by a density between about 1.0006 and 1.019 g/ml.

8. A therapeutic lipoprotein composition for intravenous administration to a subject, prepared by: mixing small unilamellar vesicles composed of phosphatidylcholine phospholipids having phase transition temperatures between about −10° and 37° C. with a mixture of apoproteins consisting essentially of apoproteins from classes A and C, under conditions effective to form lipoprotein particles composed of said vesicles and associated A and C apoproteins, wherein said mixing includes intravenously administering said vesicles to a human subject and allowing the administered vesicles to circulate in the blood stream for a period of at least 2 hours, and which further includes removing a blood sample from the subject, and isolating from serum obtained from the blood sample, lipoprotein particles having a density between about 1.0006 and 1.019 g/ml.

9. The composition of claim 8, wherein the small unilamellar vesicles have sizes between 0.02 and 0.08 microns.

10. The composition of claim 8, wherein the vesicles are composed of egg phosphatidylcholine.

11. A therapeutic lipoprotein composition comprising lipoprotein particles comprising small unilamellar vesicles composed of phosphatidylcholine phospholipids having phase transition temperatures between about −10° and 37° C. and a mixture of apoproteins consisting essentially of apoproteins from classes A and C.

12. The composition of claim 11, wherein the vesicles are empty vesicles.

13. A therapeutic lipoprotein composition comprising lipoprotein particles comprising small unilamellar vesicles composed of phosphatidylcholine phospholipids having phase transition temperatures between about −10° and 37° C. and a mixture of apoproteins consisting essentially of apoproteins from classes A and C, wherein the vesicles have sizes between 0.02 and 0.08 microns.

14. The composition of claim 11, wherein the vesicles are composed of egg phosphatidylcholine.

15. The composition of claim 11, wherein the apoproteins include apo A-1 and class C apoproteins.

16. The composition of claim 15, wherein the apoproteins are human recombinant apoproteins.

17. A therapeutic lipoprotein composition comprising lipoprotein particles comprising small unilamellar vesicles composed of phosphatidylcholine phospholipids having phase transition temperatures between about −10° and 37° C. and a mixture of apoproteins consisting essentially of apoproteins from classes A and C, wherein the lipoprotein particles are characterized by a density between about 1.0006 and 1.019 g/ml.

18. A therapeutic lipoprotein composition for intravenous administration to a subject comprising the composition of claim 11.

* * * * *